United States Patent
Johnson et al.

(10) Patent No.: US 7,141,793 B2
(45) Date of Patent: Nov. 28, 2006

(54) REMOVE VEHICLE EMISSION SENSING DEVICE WITH SINGLE DETECTOR

(75) Inventors: James H. Johnson, Tucson, AZ (US); John DiDomenico, Tucson, AZ (US)

(73) Assignee: Environmental Systems Products Holdings Inc., East Granby, CT (US)

( * ) Notice: Subject to any disclaimer, the term of this patent is extended or adjusted under 35 U.S.C. 154(b) by 682 days.

(21) Appl. No.: 09/840,080

(22) Filed: Apr. 24, 2001
(Under 37 CFR 1.47)

(65) Prior Publication Data

US 2006/0064255 A1 Mar. 23, 2006

Related U.S. Application Data

(63) Continuation of application No. 09/648,534, filed on Aug. 28, 2000, now abandoned, which is a continuation of application No. 09/480,688, filed on Jan. 11, 2000, now abandoned.

(60) Provisional application No. 60/115,537, filed on Jan. 12, 1999.

(51) Int. Cl.
 *G01N 21/35* (2006.01)
(52) U.S. Cl. .............................. 250/338.5; 250/339.13; 250/351
(58) Field of Classification Search ............ 250/339.13, 250/338.5, 351
See application file for complete search history.

(56) References Cited

U.S. PATENT DOCUMENTS

| | | | |
|---|---|---|---|
| 3,593,023 A | | 7/1971 | Dodson et al. |
| 3,655,979 A | * | 4/1972 | Jernigan, Jr. ................. 378/55 |
| 3,696,247 A | | 10/1972 | McIntosh et al. |
| 3,743,426 A | | 7/1973 | Steinberg |
| 3,860,818 A | * | 1/1975 | Stalder et al. ............... 250/343 |
| 3,908,167 A | | 9/1975 | Hulls et al. |
| 3,957,372 A | | 5/1976 | Jowett et al. |
| 3,958,122 A | | 5/1976 | Jowett et al. |
| 3,973,848 A | | 8/1976 | Jowett et al. |
| 4,160,373 A | | 7/1979 | Fastaia et al. |
| 4,390,785 A | | 6/1983 | Faulhaber et al. |
| 4,480,191 A | | 10/1984 | Karpowycz |
| 4,490,043 A | | 12/1984 | Cramp |
| 4,544,273 A | | 10/1985 | Berndt |
| 4,560,873 A | | 12/1985 | McGowan et al. |
| 4,663,961 A | | 5/1987 | Nelson et al. |
| 4,678,914 A | * | 7/1987 | Melrose et al. .............. 250/343 |
| 4,719,360 A | | 1/1988 | Kontani et al. |
| 4,746,218 A | | 5/1988 | Lord, III |

(Continued)

OTHER PUBLICATIONS

Perez-Diaz, Jose-Luis, et al., "Infrared Absorption Device for Analysis of Exhaust Gases from Moving Vehicles", part of the EUROPTO Conference on Spectroscopic Atmospheric Environmental Monitoring Techniques, *SPIE*, vol. 3493, Sep. 1998, pp. 178-183, XP-002345234.

(Continued)

*Primary Examiner*—Albert Gaglardi
(74) *Attorney, Agent, or Firm*—Pillsbury Winthrop Shaw Pittman, LLP

(57) ABSTRACT

A remote sensing device for determining at least one characteristic of a vehicle emission plume includes a radiation source, a detector, and a plurality of filters. Either the filters or the detector are movable relative to the other such that different filters, each of which is capable of filtering out radiation except radiation of a predetermined wavelength band, can be used to filter the radiation directed to the detector. Also disclosed is a method for remotely determining at least one characteristic of a vehicle emission plume using a single detector and a plurality of filters wherein either the detector or the filters are positionable relative to one another.

15 Claims, 5 Drawing Sheets

U.S. PATENT DOCUMENTS

| | | | |
|---|---|---|---|
| 4,765,961 A | 8/1988 | Schiff et al. | |
| 4,795,253 A | 1/1989 | Sandridge et al. | |
| 4,810,884 A | 3/1989 | Carlson | |
| 4,818,705 A | 4/1989 | Schneider et al. | |
| 4,829,183 A | 5/1989 | McClatchie et al. | |
| 4,924,095 A | 5/1990 | Swanson, Jr. | |
| 4,988,858 A * | 1/1991 | Pinson | 250/208.1 |
| 4,990,780 A | 2/1991 | Lee et al. | |
| 4,999,498 A | 3/1991 | Hunt et al. | |
| 5,060,505 A | 10/1991 | Tury et al. | |
| 5,099,680 A | 3/1992 | Fournier et al. | |
| 5,105,651 A | 4/1992 | Gutmann | |
| 5,129,257 A | 7/1992 | Carduner et al. | |
| 5,184,017 A | 2/1993 | Tury et al. | |
| 5,210,702 A | 5/1993 | Bishop et al. | |
| 5,246,868 A | 9/1993 | Busch et al. | |
| 5,252,828 A | 10/1993 | Kert et al. | |
| 5,306,913 A | 4/1994 | Noack et al. | |
| 5,319,199 A | 6/1994 | Stedman et al. | |
| 5,332,901 A | 7/1994 | Eckles et al. | |
| 5,343,043 A | 8/1994 | Johnson | |
| 5,371,367 A | 12/1994 | DiDomenico et al. | |
| 5,373,160 A | 12/1994 | Taylor | |
| 5,386,373 A | 1/1995 | Keeler et al. | |
| 5,401,967 A | 3/1995 | Stedman et al. | |
| 5,418,366 A | 5/1995 | Rubin et al. | |
| 5,451,787 A | 9/1995 | Taylor | |
| 5,489,777 A | 2/1996 | Stedman et al. | |
| 5,498,872 A | 3/1996 | Stedman et al. | |
| 5,572,424 A | 11/1996 | Kellogg et al. | |
| 5,583,765 A | 12/1996 | Kleehammer | |
| 5,589,629 A | 12/1996 | Quinn | |
| 5,591,975 A | 1/1997 | Jack et al. | |
| 5,621,166 A | 4/1997 | Butler | |
| 5,644,133 A | 7/1997 | Didomenico et al. | |
| 5,693,872 A | 12/1997 | Quinn | |
| 5,719,396 A | 2/1998 | Jack et al. | |
| 5,726,450 A | 3/1998 | Peterson et al. | |
| 5,731,510 A | 3/1998 | Jones et al. | |
| 5,753,185 A | 5/1998 | Mathews et al. | |
| 5,773,828 A | 6/1998 | Akiyama et al. | |
| 5,797,682 A * | 8/1998 | Kert et al. | 374/123 |
| 5,811,812 A * | 9/1998 | Williams et al. | 250/343 |
| 5,831,267 A | 11/1998 | Jack et al. | |
| 5,952,660 A * | 9/1999 | Kip et al. | 250/339.11 |

OTHER PUBLICATIONS

Technical Proposal—"Vehicle Inspection Instrumentation"; submitted to California Air Resources Board; Sep. 1, 1971, Lockheed Palo Alto Research Laboratory, Lockheed Missiles & Space Company—A Group Division of Lockheed Aircraft Corporation, Palo Alto, California.

Hoshizaki, et al., Final Report—"Vehicle Inspection Instrumentation"; submitted to California Air Resources Board; Jun. 1973, Lockheed Palo Alto Research Laboratory, Lockheed Missiles & Space Company—A Group Division of Lockhead Aircraft Corporation, Palo Alto, California.

http://www.epa.gov/otag/15-remot.htm; "Remove Sensing: A Supplemental Tool for Vehicle Emission Control," Aug. 1993, EPA 400-F-92-017, Fact Sheet OMS-15; 4 pages.

Lucien W. Chaney, "The Remote Measurement of Traffic Generated Carbon Monoxide, APCA Note-Book," Journal of the Air Pollution Association; Copyright 1983; 3 pages.

Paul Stockwell, "Tunable Diode Laser Systems Break New Ground in Water Vapour Analysis"; IMA Ltd., Unit Newall Hall Park, Otley, West Yorkshire, United Kingdom; [undated]; 8 pages.

Mark G. Allen, "Diode Laser Absorption Sensors for Gas Dynamic and Combustion Flows," Copyright 1998 Measurement Science and Technology 9; 61 pages.

Kerry L. Swayne, "Infrared Remote Sensing of On-Road Motor Vehicle Emissions in Washington State," Mar. 1999, Air Quality Program, Washington State Department of Ecology, Washington; Publication #99-204; 20 pages.

Gary A. Bishop, et al., "IR Long-Path Photometry; A Remote Sensing Tool for Automobile Emissions," 1989; reprinted from Analytical Chemistry, 61, 671A; 1989; 6 pages.

Gary A. Bishop, et al., "Oxygenated Fuels, A Remote Sensing Evaluation," SAE Technical Paper Series; Copyright 1989 Society of Automotive Engineers, Inc.; 7 pages.

Robert D. Stephens, "Remote Sensing Data and a Potential Model of Vehicle Exhaust Emissions," Nov. 1994, vol. 44, Journal of Air & Waste Management Association, pp. 1284-1292.

"An Analysis of On-Road Remote Sensing as a Tool for Automotive Emissions Control," Final Report Prepared by University of Denver Chemistry Department, Colorado, Mar. 1990; 174 pages; prepared for Illinois Department of Energy and Natural Resources.

Robert D. Stephens et al., "Remote Sensing Measurements of in-Use Vehicle Carbon Moxoxide and Hydrocarbon Exhaust Emissions," Environmental Science Department, Michigan, to be presented to Society of Automotive Engineers Government/Industry Meeting, Washington, D.C., May 15, 1991; 9 pages.

Thomas C. Austin, et al., "An Evaluation of "Remote Sensing" for the Measurement of Vehicle Emissions," prepared for The California Air Resources Board and The California I/M Review Committee, Aug 28, 1990, 30 pages; prepared by Sierra Research, Inc., California.

Robert D. Stephens, et al., "Remote Sensing Measurements of Carbon Monoxide Emissions from On-Road Vehicles," Copyright Jan. 1991, Air & Waste Management Association, vol. 42, No. 1, pp. 39-46.

Donald H. Stedman, et al., "Remote Sensing of On-Road Vehcile Emissions," Final Report to Coordinating Research Council, The University of Denver, Jan. 6, 1992, 21 pages.

Peter Popp, et al., "Development of a High-Speed Ultraviolet Spectrophotometer Capable of Real-Time NO and Aromatic Hydrocarbon Detection in Vehicle Exhaust," Department of Chemistry, University of Denver, Colorado, Prepared for Proceedings of the 7th CRC On-Road Vehicle Emissions Workshop, San Diego, California, Apr. 9-11, 1997; 10 pages.

John DiDomenico, et al., "Preliminary Results from Cold Start Sensor Testing," Presented to 7th CRC On-Road Vehicle Emissions Workshop, San Diego, California, Apr. 9-11, 1997; 1 page.

Gary A. Bishop, et al., "Enhancements of Remote Sensing for Vehicle Emissions in Tunnels," Air & Waste Management Association, vol. 44, Feb. 1994, pp. 169-175.

Paul Leonard Guenther, "Contributions to On-Road Remote Sensing of Automobile Exhaust," A Thesis Presented to the Faculty of Natural Sciences, Mathematics, and Engineering, University of Denver, Jun. 1992, 95 pages.

Donald H. Stedman, et al., "On-Road Remote Sensing of CO and HC Emissions in California," Prepared for Research Division, California Air Resources Board, Sacramento, CA, submitted by University of Denver Chemistry Department, Feb. 1994, 136 pages.

"Unstaffed On-Road Emissions Measurements Systems Services," Prepared by Parsons Engineering Science, Inc., Pasadena, California, Sep. 1995.

"Proposal/Quote for Unstaffed On-Road Emissiosn Measurements Systems Services" in response to Phase IV—RFQ #94/95-003, prepared by Remote Sensing Technologies, Inc. delivered to Department of Consumer Affairs, Bureau of Autromotive Repair, Sacramento, California, Sep. 1, 1995.

Steven H. Cadle, et al., "Measurement of Exhaust Particulate Matter Emissions from In-Use Light-Duty Motor Vehicles in the Denver, Colorado Area," Final Report, prepared for Coordinating Research Council, Atlanta, Georgia, Dec. 9, 1997, prepared by General Motors R&D Center, Michigan; 20 pages.

Steven H. Cadle, et al., "Measurement of Exhaust Particulate Matter Emissions from in-Use Light-Duty Motor Vehicles in the Denver, Colorado Area," Final Report, prepared for Coordinating Research Council, Atlanta, Georgia, Mar. 24, 1998, "Appendix E. University of Denver Remote Sensing Observation of Smoking Vehicles," prepared by General Motors R&D Center, Michigan; 20 pages.

Robert D. Stephens, et al., "Remote Sensing of Carbon Monoxide Emissions from On-Road Vehicles," Environmental Science Department, General Motors Research Laboratories, Michigan for presentation to Air and Waste Management Association, NC, May 1, 1990, 46 pages.

"Description and Documentation for Interim Vehcile Clean Screening Credit Utility," Draft Report, United States Environmental Protection Agency, May 1998, 40 pages.

David S. E. Petherick, "Ontario's Indoor, Controlled-Mode Remote Sensing I/M Prescreen Concept," Ministry of Transportation of Ontaro, Copyright 1996 Society of Automotive Engineers, Inc., 9 pages.

P. A. Walsh, et al., "Texas 1996 Remote Sensing Feasibility Study," Final Report, prepared for Texas Natural Resource Conservation Commission, Austin, Texas, Aug. 29, 1997, prepared by Desert Research Institute, Energy and Environmental Engineering Center, Reno, Nevada, 9 pages.

"On Road Emissions Measurement System—Specifications," Bureau of Automotive Repair, Aug. 30, 1999, Revision—J, 15 pages.

Craig S. Rendahl, "Further Analysis of Wisconsin's Remote Vehicle Emissions Sensing Feasibility Studies," "Quality Control Efforts of Remote Vehicle Emissions Sensing," and "Data Handling and Validation from Wisconsin's Remote Vehicle Emissions Sensing Studies," Presented at the Air & Waste Management Annual Measurement of Toxics and Related Pollutants Conference, Research Triangle Park, North Carolina, May 1996, 34 pages.

James D. Peterson, et al., "Find and Fix the Polluters," Chemtech, Jan. 1992, Copyright 1992 American Chemical Society, 7 pages.

RSD 1000 Operator's Manual (Preliminary), Remote Sensing Technologies, IFB No. 94019, Jun. 1993, 66 pages.

RSD-1000 Remote Sensing Device Information Package to Mr. Wolf Klassen, Department of Natural Resources, Presented by Dennis L. Smith, Feb. 24, 1993, 123 pages.

Robert D. Stephens, et al., "An Experimental Evaluation of Remote Sensing-Based Hydrocarbon Measurements: A Comparison to FID Measurements", *Journal of the Air & Waste Management Association*, vol. 46, Feb. 1996, pp. 148-158.

Donald H. Stedman, "Automotive Carbon Monoxide Emission," *Environmental Science & Technology*, vol. 23, No. 2, 1989, pp. 147-149.

Masayuki Adachi, et al., "Automotive Emission Analyses Using FTIR Spectrophotometer," Published by the Society of Automotive Engineers, SAE# 920723, pp. 820-827.

Michael D. Koplow, et al., "Characterization of On-Road Vehicle NO Emissions by Means of a TILDAS Remote Sensing Instrument", Published by the Coordinating Research Council, Published for the 7th CRC On-Rod Vehcile Emissions Workshop, Mar. 11, 1997, pp. 1-25.

Scott E. McLaren, et al., "Comparison of an Open Path UV and FTIR Spectrophotometer", Published by the Air & Waste Management Association, Published for Presentation at the 85th Annual Meeting & Exhibition, Kansas City, Missouri, Jun. 21-26, 1992, pp. 1-10.

"Developing an Inspection/Maintenance Program for Alternatively-Fueled Vehicles", Third Interim Report Submitted to the California Bureau of Automotive Repair, Submitted by Radian Corporation, Apr. 20, 1993, 147 pages.

Iain Frederick McVey, "Development of a Remote Sensor for Mobile Source Nitric Oxide", A Thesis Presented to the Faculty of Natural Sciences, Mathematics, and Engineering, University of Denver, Nov. 1992, 111 pages.

S. P. Beaton, et al., "Emission Characteristics of Mexico City Vehicles", *Journal of the Air & Waste Management Association*, vol. 42, No. 11, Nov. 1992, pp. 1424-1429.

Douglas R. Lawson, et al., "Emissions from In-Use Motor Vehicles in Los Angeles: A Pilot Study of Remote Sensing and the Inspection and Maintanance Program", *Journal of the Air & Waste Management Association*, vol. 40, No. 8, Aug. 1990, pp. 1096-1105.

Yi Zhang, et al., "Enhancement of Remote Sensing for Mobile Source Nitric Oxide", *Journal of the Air & Waste Management Association*, vol. 46, Jan. 1996, pp. 25-29.

Donald H. Stedman, et al., "Evaluation of a Remote Sensor for Mobile Source CO Emissions", U.S. Environmental Protection Agency, CR-815778-01-0, Report No. EPA/600/4/-90/0232, Jan. 1991, 90 pages.

James Butler, et al., "Factors Affecting the NDIR Measurement of Exhaust Hydrocarbons", Published by the Coordinating Research Council, Published for the CRC 5th On-Road Vehicle Emissions Workshop, 1995, 16 pages.

Scott E. McLaren, et al., "Flux Measurements Using Simultaneous Long Path Ultraviolet and Infrared Spectroscopy", Published by the Air & Waste Management Association, Published for Presentation at the 83rd Annual Meeting & Exhibition, Pittsburgh, Pennsylvania, Jun. 24-29, 1990, 7 pages.

Gary A. Bishop, et al., "Infrared Emission and Remote Sensing", *Journal of the Air & Waste Management Association*, vol. 42, No. 5, May 1992, pp. 695-697.

Hakan Axelsson, et al., "Measurement of Aromatic Hydrocarbons with the DOAS Technique", *Applied Spectroscopy*, vol. 49, No. 9, 1995, pp. 1254-1260.

Gary A. Bishop, et al., "Method Comparisons of Vehicle Emissions Measurements in the Fort McHenry and Tuscarora Mountain Tunnels", *Atmospheric Environment*, vol. 30, No. 12, 1996, pp. 2307-2316.

Donald H. Stedman, et al., "NOx Data by Remote Sensing", Published by the Coordinating Research Council, Published for the 5th CRC On-Road Vehicle Emissions Workshop, Apr. 3-5, 1995, 16 pages.

Donald H. Stedman, et al., "On-Road Carbon Monoxide and Hydrocarbon Remote Sensing in the Chicago Area", Final Report Prepared by University of Denver Chemistry Department, Prepared for Illinois Department of Energy and Natural Resources, Office of Research and Planning, Illinois Contract AQ 40, Project 91/122, Report No. ILENR/RE-AQ-91/14, Oct. 1991, pp. 1-70.

Gary A. Bishop, et al., 'On-Road Carbon Monoxide Emission Measurement Comparisons for the 1988-1989 Colorado Oxy-Fuels Program', *Environmental Science & Technology*, vol. 24, No. 6, 1990, pp. 843-847.

Donald H. Stedman, et al., "On-Road CO Remote Sensing in the Los Angeles Basin", Final Report Prepared for the Research Division, California Air Resources Board, Submitted by University of Denver Chemistry Department, Aug. 1991, Contract No. A932-189, 70 pages.

Scott McLaren, "Open Path Spectrometers for Atmospheric Monitoring", A Dissertation Presented to the Faculty of Natural Sciences, Mathematics and Engineering, Nov. 1995, 170 pages.

Carol E. Lyons, et al., "Remote Sensing Enhanced Motor Vehicle Emissions Control for Pollution Reduction in the Chicago Metropolitan Area: Siting and Issue Analysis", Final Report Prepared by University of Denver Atmospheric Science Center, Prepared for Illinois Department of Energy and Natural Resources, Office of Research and Planning, Illinois Contract AQ 30, Project 90/009, report ILENR/RE-AQ-91/15, Oct. 1991, pp. 1 -65.

Peter John Popp, "Remote Sensing of Nitric Oxide Emissions from Planes, Trains and Automobiles", A Dissertation Presented to the Faculty of Natural Sciences, Mathematics and Engineering, Aug. 1999, 170 pages.

Brett C. Singer, et al., "Scaling of Infrared Remote Sensor Hydrocarbon Measurements for Motor Vehicle Emission Inventory Calculations," *Environmental Science & Technology*, vol. 32, No. 21, 1998, pp. 3241-3248.

Lucian W. Chaney, "The Remote Measurement of Traffic Generated Carbon Monoxide", *Journal of the Air Pollution Control Association*, vol. 33, No. 3, Mar. 1983, pp. 220-222.

Jose Luis Jimenez-Palacios, "Understanding and Quantifying Motor Vehicle Emissions with Vehicle Specific Power and TILDAS Remote Sensing", A Dissertation Presented to the Department of Mechanical Engineering, Feb. 1999, 360 pages.

"Vehicle Inspection Instrumentation", Published by the Lockhead Missiles and Space co., Inc., Report No. ARB-R-643-73-26, Jun. 30, 1973, 99 pages.

John E. Sigsby, Jr., et al., "Volatile Organic Compound Emissions from 46 In-Use Passenger Cars", *Environmental Science & Technology*, vol. 21, No. 5, 1987, pp. 466-475.

Yi Zhang, et al., "Worldwide On-Road Vehicle Exhaust Emissions Study by Remote Sensing", *Environmental Science & Technology*, vol. 29, No. 9, 1995, pp. 2286-2294.

* cited by examiner

REMOVE VEHICLE EMISSION SENSING DEVICE WITH SINGLE DETECTOR

CROSS-REFERENCE TO RELATED APPLICATIONS

This application is a continuation of U.S. patent application Ser. No. 09/648,534, filed Aug. 28, 2000 (abandoned), which is a continuation of U.S. patent application Ser. No. 09/480,688, filed Jan. 11, 2000 (abandoned), which claims priority to U.S. Provisional Patent Application Ser. No. 60/115,537, filed Jan. 12, 1999.

FIELD OF THE INVENTION

The present invention relates generally to filter/detector arrangements for use in remote vehicle emissions analysis and remote sensing devices.

BACKGROUND OF THE INVENTION

Remote sensing devices may be used to detect and characterize emissions from a vehicle. One device for performing such a process analyzes radiation that passes through the vehicle emission using a detector. Various components of the vehicle emission absorb radiation of specific characteristic wavelengths. A filter is used to permit only a radiation band including the characteristic wavelength of interest to reach the detector. If multiple components of the emission are to be analyzed in this manner, multiple sets of detectors and filters are generally necessary to carry out such measurements.

A known device for the remote sensing of vehicle emissions is depicted in FIG. 1. A beam (1) from a radiation source (7) passes through emissions plume (8) of vehicle (9) and is reflected from mirror (2) onto reflecting wheel (3). Beam (1) is then reflected from reflecting wheel (3) to one of a group of CD mirrors (4). The group of mirrors (4) focus and reflect the beam (1) through respective filters (5) and onto respective detectors (6). One such remote sensing device is disclosed in U.S. Pat. No. 5,210,702.

Such devices, however, may have certain drawbacks. These devices may have a large number of parts to manufacture, assemble, align, maintain, and calibrate, including special reflectors, multiple detectors and multiple light filters. Each of these parts introduces error into the final measurements. For example, light filters may suffer from light bleed, allowing undesirable wavelengths of light to reach the detectors. Uncertainty as to the measurements may also occur because different detectors may react differently to the variety of conditions encountered during the use of these devices.

Additionally, use of multiple filters, detectors, reflectors, and the like can add considerable complexity and bulk to the device. Also, if other components of the emission are to be detected, the replacement of filters and/or detectors to provide suitable filters and detectors for such other components may involve considerable cost in parts, as well as in assembly, alignment, and calibration of the device.

Another gas analysis device is disclosed in U.S. Pat. No. 4,678,914. This device employs an infrared (IR) gas analyzer in which IR radiation from a source is directed toward an IR detector. The IR radiation passes through both a gas located in a sample cell and then one of various light filters mounted on a continuously rotating filter wheel. This device requires close proximity to an emissions output in order to operate properly, and employs a sample chamber for gas analysis. Devices which employ a gas sample chamber are not feasible for remote sensing of vehicle emissions because of the need to collect a sample of the emission and isolate it in the gas sample chamber. Also, such devices only provide a localized reading of the gas at the exact point where the sample is taken.

These and other drawbacks of known devices exist.

SUMMARY OF THE INVENTION

An object of the present invention is to overcome these and other drawbacks in existing devices.

Another object of the present invention is to provide greater flexibility in remote vehicle emissions sensing devices by allowing multiple different components to be detected without using multiple detection units.

Another object of the present invention is to provide greater accuracy and certainty in remote vehicle emissions sensing devices by reducing the number of detectors used in such devices to thereby reduce uncertainty caused by use of several different detectors under changing ambient conditions.

One aspect of the present invention provides a device including a radiation source, a detector, and a plurality of filters. A beam from the radiation source passes through the emission plume of a vehicle, and one of the plurality of filters which is aligned with the detector to the detector. When a different component of the emission is to be analyzed, the filter which is aligned with the detector is changed and the detection process is repeated.

Another aspect of the invention provides a method for remotely sensing vehicle emissions by passing a beam from a radiation source through a vehicle emission plume and one of a plurality of filters which is aligned with a detector to the detector. The method may also include the step of moving the filters to align different filters with the detectors or moving the detector to allow the detector to be aligned with different ones of the filters.

Other aspects and advantages of the invention will be apparent from the detailed description of the preferred embodiments which follows.

DETAILED DESCRIPTION OF THE PREFERRED EMBODIMENTS

Figure 2A:
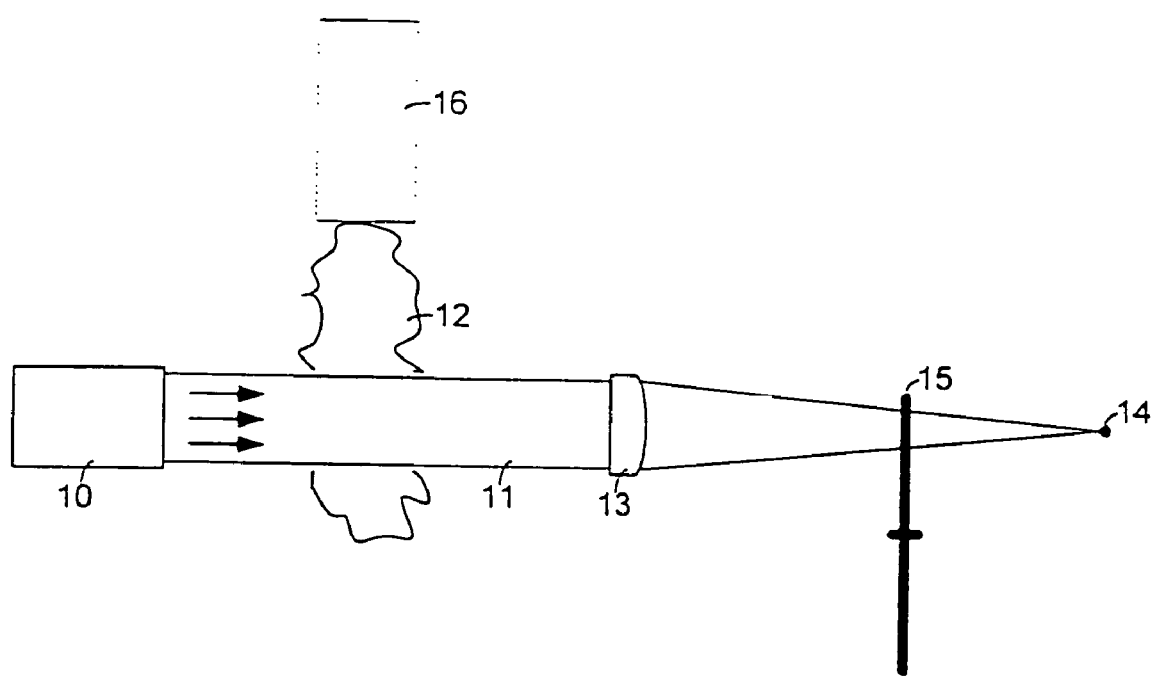
FIG. 2a illustrates an embodiment of a remote vehicle emissions sensing device of the present invention.
Figure 2B:
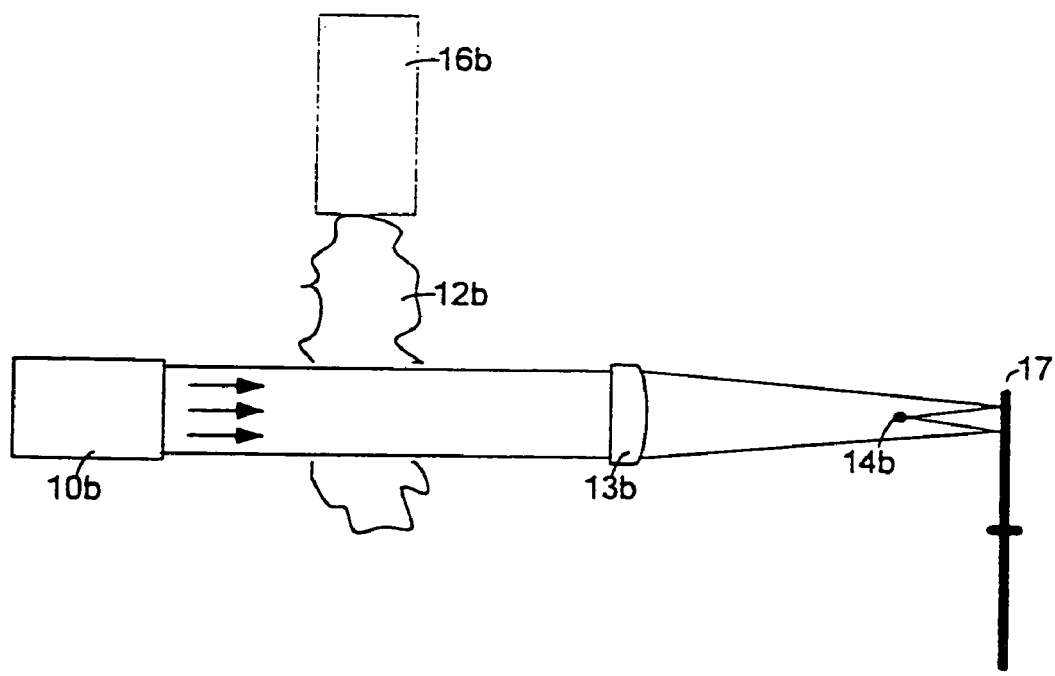
FIG. 2b illustrates another embodiment of a remote vehicle emissions sensing device of the present invention.

The present invention, as illustrated in FIGS. 2a and 2b, is intended for use in a system for the remote sensing of vehicle emissions, whereby a variety of different components of the vehicle emission are sensed by passing a beam of radiation through the vehicle emission plume. After passing through the emission plume, the beam, which may include ultraviolet radiation and/or infrared radiation, is received by a detector. The concentrations of various components of the vehicle emission plume may be calculated by determining the amount of radiation of certain characteristic wavelengths which has been absorbed from the beam by the emission components of interest upon passage through the vehicle emission plume.

FIG. 2a illustrates one embodiment of a remote sensing device ("RSD") in accordance with the present invention. A beam (11) from a radiation source (10) passes through an emission plume (12) of a vehicle (16). The beam (11) may optionally be focused on a detector (14) by lens (13). The light beam (11) also passes through a set of moveable filters (15) before it impinges on detector (14).

In the present invention, moveable filters (15) allow a single detector (14) which has a broad enough frequency response to cover all of the detection bands of interest, to measure different components of the vehicle emission plume. Alternatively, two or more detectors (14) can be employed to cover all of the detection bands of interest. Each filter (15) permits only a certain detection band of radiation to reach the detector (14). Filters (15) may be pass through filters, which allow transmission of only certain wavelengths through the filters (15). Each of the various filters (15) is used to isolate different detection bands of radiation for detection of different components of the vehicle emission. Each detection band is carefully selected to be centered about a wavelength of radiation that is characteristic of the absorption pattern of a to specific component of the vehicle emission. In this manner, radiation characteristic of each component of the vehicle emission can be isolated and impinged at different times upon the same detector (14).

The filters (15) may be moved so that one filter (15) at a time is aligned with only a single detector (14). The alignment is such that all radiation to be received by the detector (14) must first pass through the aligned filter (15). A single RSD may be employed to detect multiple components of a vehicle CD emission without requiring more than one detector (14) because the present invention allows a plurality of different detection bands to be directed to a single detector (14) using a moveable set of filters (15).

In another embodiment shown in FIG. 2b, a movable set of reflective filters (17) is used. A beam (11b) from a radiation source (10b) passes through an emission plume (12b) of a vehicle (16b). The beam (11b) may optionally be focused on a detector (14b) by lens (13b) via reflection off of one or more of a moveable set of reflective filters (17). Reflective filters (17) may reflect only the wavelengths of specific detection bands of radiation for detection of different components of vehicle emission plume (12b).

Figure 3:
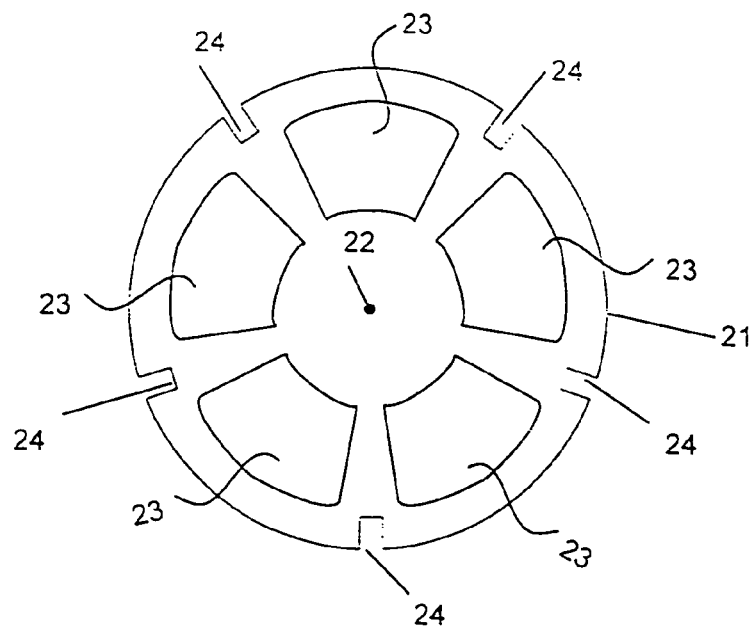
FIG. 3 illustrates a wheel with filters mounted thereon which may be employed in accordance with the present invention.

In an embodiment shown in FIG. 3, the moveable set of filters (23) may comprise a rotating filter wheel with filters mounted on the wheel. As illustrated in FIG. 3, the filter wheel (21) is mounted for rotation about its axis (22). Various filters (23) are mounted on the filter wheel (21). Thus, in this embodiment, the filter wheel (21) may be rotated on its axis to align different filters (23) with a single detector at different times. As noted previously, each filter (23) permits only a specific detection band of radiation to reach the detector by transmission or reflection. Each detection band is centered on a wavelength of radiation that is characteristic of the absorption pattern of a specific component of the vehicle emission. Each filter (23) on the wheel (21), passes a detection band of radiation which corresponds to a specific vehicle emission component to be detected. The wheel (21), and therefore the filters (23), rotate so that multiple vehicle emission components may be sequentially detected and analyzed using a single detector.

The filter wheel (21) may be provided with a plurality of notches (24) which may periodically activate an optical switch (not shown) whereby the processor (19) can associate a particular detector reading with a particular one of filters (23) so that the reading can be linked to the component of the exhaust being measured. Any other suitable means for informing the processor (19) which filter (23) is associated with a particular detector reading may be employed. For example, the filter wheel (21) may be rotated stepwise and for each step of rotation a signal may be sent to the processor.

Preferably, one of the filters (23) corresponds to a reference channel having a transmission bandwidth centered at a wavelength of 3.9 microns. This reference channel can be employed to determine background noise and/or exhaust opacity, if desired.

Figure 4:
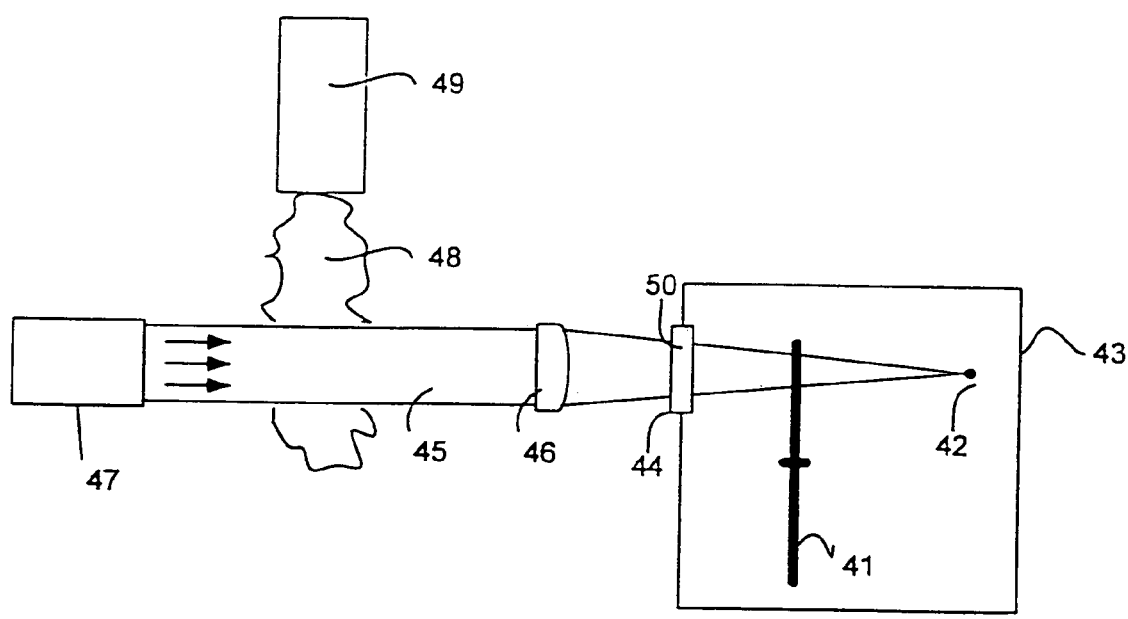
FIG. 4 illustrates moveable filters and a detector located in a sealed housing according to another embodiment of the present invention.

In another embodiment of the invention shown in FIG. 4, moveable filters (41) and a detector (42) are placed in a sealed housing (43). By placing moveable filters (41) and a detector (42) in a sealed housing (43), undesired radiation may be prevented from impinging on the detector (42) or entering the filters (41). The sealed housing (43) may have, for example, a single opening (44) to allow a beam (45) from a source (47) to enter after passing through vehicle emissions plume (48) of vehicle (49). As illustrated in other embodiments, a focusing mirror (46) may be used to focus beam (45) onto the detector (42). Moveable filters (41) and a detector (42) may be aligned in such a manner as to receive beam (45) at the detector (42) through a single one of filters (41).

In another embodiment of the invention, a general filter (50) may be placed in the path before the detector to prevent unwanted radiation from reaching the detector. A general filter (50) may be used, for example, to eliminate radiation outside a broad detection band which includes radiation of wavelengths within a series of narrower detection bands specific to each of the components of interest. The general filter (50) may alternatively be employed to filter out specific radiation components such as all visible light, all ultraviolet light, etc. In one embodiment of the invention, a beam from the radiation source includes radiation having wavelengths in the broad detection band of 3 to 6 microns, and a general filter (50) may be configured to prevent all other light from reaching the detector (42) and/or the filters (41). Thus, a general filter (50) may be placed at the single opening (44) of a sealed housing (43). Movable filters (41) are then aligned so that a beam (45) impinging on the detector (42) passes through a desired one of filters (41) before reaching the detector (42).

Figure 5:
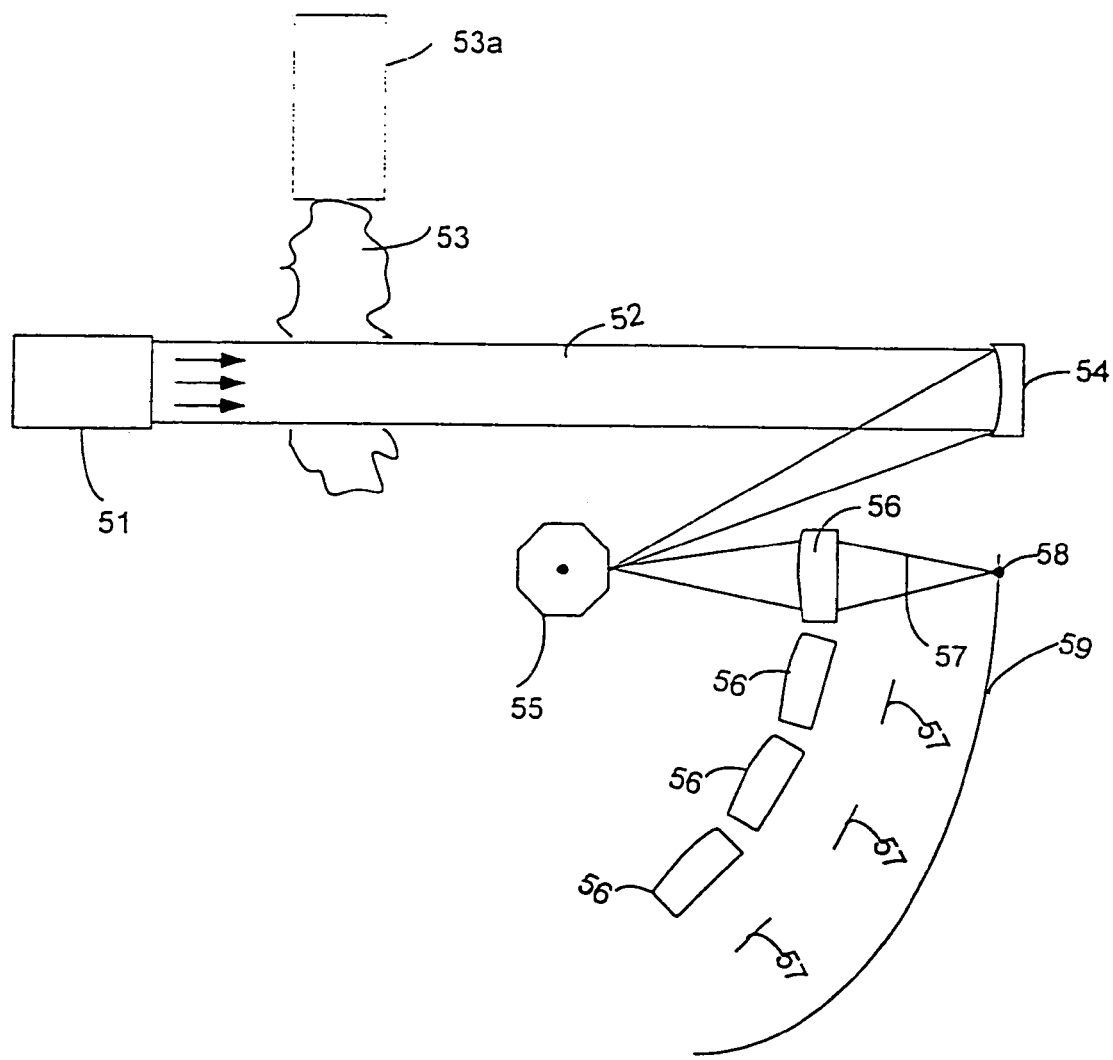
FIG. 5 illustrates another embodiment of a remote vehicle emissions sensing device of the present invention.

Other embodiments of the invention are also envisioned. In a further alternative embodiment (not shown), the moveable filters (41) slide into alignment with the detector (42). In another embodiment, the filters are stationary, and the detector (42) may be moved to align it with the appropriate filter. As illustrated in FIG. 5, a beam (52) from radiation source (51) passes through a vehicle emission plume (53) of a vehicle (53a). Beam (51) reflects off of mirror (54) onto reflecting wheel (55). Reflecting wheel (55) directs beam (51) through respective focusing lenses (56) to focus the beam (51) through filters (57) and onto detector (58). Detector (58) is moveable in slot (59) so that it may be aligned with the appropriate one of filters (57). Other variations on this embodiment of the invention are also possible.

A method of remotely sensing vehicle emissions is also contemplated in the present invention. Using the structure of the present invention, vehicle emissions may be sensed by emitting radiation from a radiation source and passing the radiation through a vehicle emission plume. The method is continued by passing radiation through one of a plurality of filters, receiving the radiation at a detector, and determining the concentration of one or more components of the vehicle emissions from the detector response.

As noted previously, the filters may be located on a wheel mounted for rotation about its central axis. In one embodiment of the invention, the wheel rotates at a constant speed. In another embodiment of the invention, the wheel only rotates when a vehicle emission plume is present in the light beam.

Figure 1:
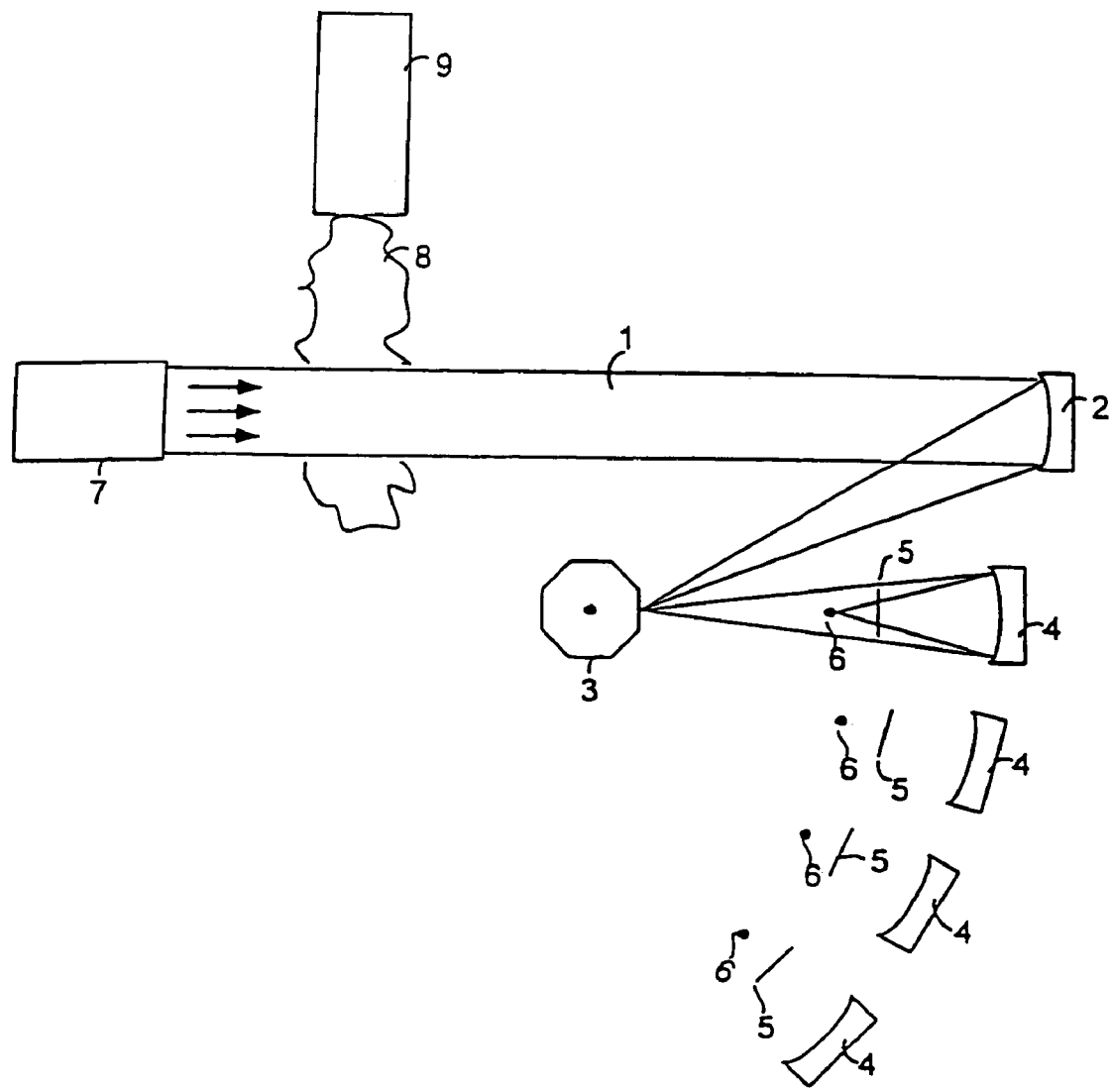
FIG. 1 illustrates a known remote vehicle emissions sensing device.

The present invention improves on known devices by eliminating the need for multiple sets of filters and corresponding detectors, and reducing the number of parts needed. Use of moveable filters or a moveable detector may eliminate the need for multiple detectors, (6), multiple mirrors, (4), and a reflecting wheel, (3), which are employed in the conventional device shown in FIG. 1. Additionally, multiple vehicle emission components may also be determined without having to align a reflecting wheel (3), multiple mirrors (4), multiple filters (5), and multiple detectors (6). As illustrated in FIG. 2, the beam (11) may be directed through one of the moveable filters (15) which is currently aligned with the detector (14). This saves time, effort, and expense when manufacturing and repairing the RSD. Additionally, filter wheel (15) may be easily changed, thus allowing a series of different components in the vehicle emission to be detected by providing a series of new filters which permit passage of radiation within the appropriate detection bands for the different components.

The RSD of the present invention allows detection of vehicle emissions in an open area. There is no need for a cell or chamber in which to gather the emission plume to determine the concentrations of various components thereof. Further, this configuration allows a single RSD of the present invention to sequentially sense the vehicle emissions of multiple vehicles over a short time span to thereby make remote roadside vehicle emission sensing practicable.

Further, the RSD unit of the present invention may be a mobile RSD which is capable of being moved to a number of locations. In one embodiment, the RSD is placed at an exit ramp of a highway, and is used to remotely determine components of vehicle emissions. Some time later, the RSD may be moved to a different location and employed at the new location to sense the same or different components of vehicle emissions.

Figure 6:
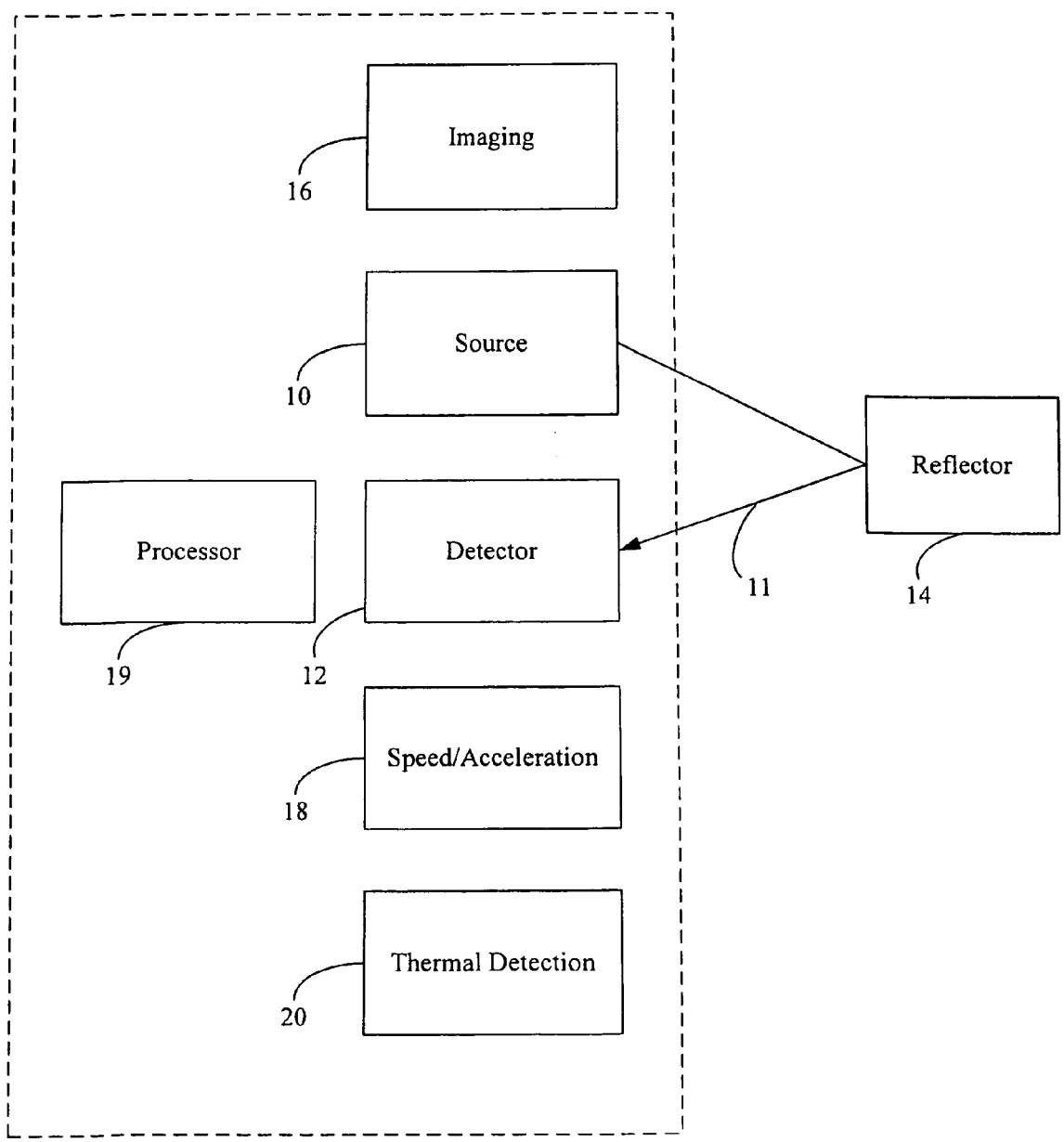
FIG. 6 shows a schematic block diagram of the components of an embodiment of a remote vehicle emission sensing device in accordance with the present invention.

FIG. 6 illustrates a schematic representation of components of a RSD in which the present invention may be employed. Embodiments of the invention may include some or all of the various components as described below.

Radiation Source

Preferably, an RSD unit comprises a source of electromagnetic radiation 10 which may be used in the absorption spectroscopy measurement of vehicle exhaust emissions. Preferably, source 10 may comprise an infrared (IR) radiation source producing beam 11. Some embodiments of the RSD may include other types of radiation sources, for example, an ultraviolet (UV) source, a visible light source, or a combination of sources.

Radiation Detector

The RSD unit may further comprise a detector 12 of electromagnetic radiation. The detector 12 is preferably chosen to permit detection of electromagnetic radiation emitted by the source. For example, the detector 12 may comprise a photodetector (e.g., a photodiode), a photomultiplier tube (PMT), a spectrometer or other suitable radiation detector. For embodiments using ambient radiation sources an appropriately sensitive detector may be used. For example, a mercury cadmium telluride (Hg Cd Te) photodetector may be used to detect ambient IR radiation. Other detectors are possible.

Reflector

According to one embodiment, the RSD unit may comprise a reflector 14 mounted in a manner to allow radiation from the source 10 to be reflected into the detector 12 for analysis. The reflector 14 may comprise a mirror, prism, diffraction grating, beam splitter or other device suitable for reflecting the radiation of the source 10. The reflector 14 may form part of the detection unit in which case the reflector 14 may function to split the radiation beam among one or more detectors, focus the radiation beam onto one or more detectors or redirect the radiation beam to the appropriate detection for detection of a particular species. In addition, plural reflectors 14 may be employed to accomplish one or more of these functions in any combination.

In another embodiment the reflector 14 may comprise a lateral transfer mirror used to reflect the source 10 radiation back along a path displaced laterally (or vertically) from the path between source 10 and reflector 14. In this embodiment, the reflector generally does not form part of a detection unit but rather is located remotely from the detection unit. The primary purpose of transfer mirrors is to redirect the radiation to the detector unit. A variety of different transfer mirrors may be employed in the RSD unit depending primarily upon the particular spatial relationship of the radiation source 10, detector 12 and reflector 14 which is to be employed by the RSD unit. Several configurations are described below, some of which require different types of transfer mirrors to redirect the radiation beam to the detector unit.

Imaging Unit

The RSD unit may also include an imaging unit 16 which may be used to capture or record an image of a vehicle passing through the detection system. The imaging unit 16 may be arranged to record an image of a vehicle at a specified location in the detection system. The imaging unit 16 may comprise, for example, a camera, such as a film, video or digital camera. Other imaging devices may also be used.

Preferably, the imaging unit 16 may record an image of the vehicle identification tag (i.e., license plate). Tag information may be processed, using a suitable data processor, to identify additional information about the respective vehicle. For example, Motor Vehicle Department databases may be accessed to retrieve vehicle owner information, vehicle make, model type, model year and other information. In some embodiments, this additional information may be incorporated into the emission sensing data analysis. For example, the make and model year of the vehicle may be used to input information (e.g., whether the vehicle includes a carburetor or fuel injector, etc.) into certain data processing routines.

Speed and Acceleration

The RSD unit may also include a speed and acceleration detection unit 18. Preferably, a vehicle's speed and acceleration through the detection system may be measured using speed detection unit 18. For example, the speed detection unit may comprise an arrangement of laser beams associated with timing circuitry. The arrangement of laser beams may be arranged to traverse the path of a vehicle at various points in the detection system. As a vehicle passes through the detection system it will cause interruptions in the laser beams. The times at which the beam interrupts occur may be used to calculate the vehicle's speed and acceleration. Other methods of detecting vehicle speed and acceleration may also be used. For example, radar systems or transducers (or piezoelectric elements) may be placed at locations in the roadway to monitor vehicle passage through the system. Preferably, the speed and acceleration data may be input into a data processing unit 19 to accurately characterize vehicle operation conditions (e.g., accelerating or decelerating). Other uses of the speed and acceleration data are also possible.

Thermal Detection Unit

Some embodiments of the invention may incorporate a thermal detection unit 20. Preferably, the thermal detection unit 20 may comprise a non-contact thermometer system. For example, an IR thermometer may be used to optically detect the temperature of remote objects. Other temperature detection systems may also be used.

Preferably, the thermal detection unit is used to detect the temperature of portions of the vehicle passing through the RSD system. Some embodiments may use direct sensing of the area of interest. For example, an IR thermometer may be aimed at the underside of a passing vehicle to detect the temperature(s) of vehicle components (e.g., engine, catalytic converter, muffler, etc.). Indirect sensing may also be used. For example, an IR thermometer may be aimed at the roadway to measure the heat reflected from the underside of a vehicle.

Preferably, the thermal information recorded by the thermal imaging unit 20 may be incorporated into the processing for the vehicle emission data. For example, a temperature reading of a vehicle's engine may indicate that the engine has just recently been started (i.e., the engine is "cold" or has not reached normal operating temperature). Such a cold engine reading may initiate alternative data processing for the emission data.

Data from thermal detection unit 20 may also be used for other data handling procedures. For example, it may be preferable to identify whether a vehicle's catalytic converter is operational. A temperature reading indicating that the catalytic converter is "cold" may indicate that the converter is not functioning. However, a cold catalytic converter might also indicate that the vehicle has only been driven for a short period and, thus, has not achieved operational temperature. Embodiments of the present invention reduce the chance of such a potentially misleading reading by detecting the temperature of other portions of the vehicle. For example, a temperature reading indicating that the catalytic converter is cold, but the brake rotor (or engine) is "hot" indicate with greater certainty, that the vehicle has reached operating temperature and the catalytic converter is indeed non-operational. Other uses for collected thermal data are also possible.

Thermal detection unit 20 may comprise various detection apparatus configurations. For example, two thermal detectors may be arranged to view a vehicle traveling in a traffic lane. Preferably, the thermal detectors are positioned at points affording different angles of view at the vehicle. The thermal detectors may be positioned near the locations of speed and acceleration detection units (i.e., spaced with some distance between detectors). Spatial separation of the detectors and use of different angles of view increase the likelihood of detecting the temperature of the areas of interest on the vehicle (e.g., the engine, catalytic converter, etc.) and also afford a time sequence of measurements (i.e., the vehicle crosses one detector, then the other at a later time). In some embodiments, an additional thermal detector may be incorporated. The additional thermal detector may be positioned at a suitable location to detect the temperature of the front of the vehicle (e.g., the radiator or engine). For example, the additional thermal detector may be positioned at either side of the lane at a sufficient height to detect the front of the vehicle, or be embedded into the lane to record a head-on view of the vehicle.

Some embodiments may include arrays of thermal detectors to achieve an even greater likelihood of detecting the desired temperature readings. For example, in an embodiment incorporating an IR thermometer, an array of detection beams may be aimed at the vehicle. The array may span vertical and horizontal regions. Using such an array of detection beams allows the thermal detection unit 20 the ability to detect the temperature of vehicles of varying size and shape. In addition, some of the beams in the array may be used to detect reflected heat off of the lane. Using an array of detector beams may also result in greater accuracy in temperature measurements. The focal point of each detection beam in the array can be narrowed to detect the temperature of a smaller region of interest. In this manner, a more accurate temperature of each point may be obtained. For example, a detector beam with a focal point four inches in diameter will take an average temperature over the whole four inch region within the focal point. If the region of interest happens to be a one inch exhaust pipe on a vehicle, the detector will average the temperature of the region of interest (i.e., the pipe comprising one-fourth of the focal region) with objects outside of the region of interest (i.e., the other three fourths of the focal region) resulting in a less accurate temperature reading. In contrast, an array of smaller focal point detector beams (e.g., one inch in diameter each) will be more likely to detect an accurate temperature of the region of interest (e.g., a one inch exhaust pipe).

These and other thermal detection techniques may be used advantageously in a remotely operated unit, but are not limited to such use. They may also be used in other RSD systems as well.

Processing Unit

The RSD unit preferably includes a data processing unit 19 to carry out analysis of detected data, among other things. The processing may be accomplished using a suitable processing device, for example, a computer or other microprocessor. The processing unit 19 may include software to accomplish desired analysis of collected data. For example, the software may be used to calculate the concentrations of various exhaust gas constituents (e.g., HC, $CO_2$, $NO_x$, CO, etc.), the decay rate (e.g., dissipation in time) of the exhaust constituents, the opacity of the exhaust plume, the temperature, speed and acceleration of the vehicle, and other calculations. In one embodiment, software may be used to calculate detected ratios between $CO_2$ and other exhaust components. The software may make comparisons to threshold concentration values or emission profiles for characterization of vehicles as high or low emitting vehicles and to ensure compliance with predetermined emission standards.

The processing unit may also comprise software routines to accomplish other data analysis functions. For example, the vehicle emission data may be checked for running losses. Running losses may typically include emission readings due to fuel system leaks on a vehicle (e.g., leaky fuel tank filler cap, fuel line, etc.), blow by emissions (i.e., emissions due to other vehicles in the vicinity) or other systematic losses.

The data processing may also include software routines to accomplish various vehicle owner notification processes. For example, a vehicle owner of a vehicle that has been recorded as "clean" (i.e., in compliance with certain predetermined emission levels) may, upon a second recording of "clean," receive notification of the fact. Coordination with local authorities may be arranged to grant vehicle owners a waiver or pass of local emission certification procedures upon receiving such clean notification. Likewise, owners of vehicles that fail to meet predetermined emission levels may receive notification requiring the owner to remedy the non-compliance. Other data processing functions are possible.

Other embodiments and uses of the invention will be apparent to those skilled in the art from consideration of the specification and practice of the invention disclosed herein. The specification and examples should be considered exemplary only. The scope of the invention is to be determined by the claims appended hereto.

What is claimed is:

1. A gas analysis device for remotely determining concentrations of at least two exhaust gas constituents in a vehicle emission plume, comprising:
   a radiation source which directs radiation through an emission plume of a moving vehicle;
   at least two filters, arranged on a rotatable filter wheel, that are sequentially positionable to receive the radiation from the radiation source after the radiation has passed through the emission plume of the vehicle, wherein each of the at least two filters is capable of filtering out radiation except for a predetermined wavelength band; and
   a detector positioned such that radiation from the radiation source may be sequentially directed onto the detector via the at least two filters to thereby produce at least two detector responses proportional to the intensity of radiation directed onto the detector via the at least two filters.

2. The device according to claim 1, wherein the filter wheel and the detector are housed in a housing which is sealed to substantially prevent radiation from reaching the detector except via one of the at least two filters.

3. The device according to claim 1, further comprising a general filter that removes substantially all visible light from a radiation beam passed there-through, wherein the general filter is positioned such that a beam from the radiation source passes through the general filter after passing through the emission plume of the vehicle but before reaching the detector.

4. The device according to claim 1, wherein one of the at least two filters comprises a reflective filter.

5. The device according to claim 1, wherein one of the at least two filters comprises a pass through filter.

6. The device according to claim 1, wherein the radiation source projects a beam of infrared radiation across the path of the moving vehicle.

7. The device according to claim 1, further comprising a processor for processing the at least two detector responses to provide information about the composition of the emission plume of the moving vehicle.

8. The device according to claim 7, further comprising an indicator for informing the processor which of the at least two filters is optically aligned with the detector for a particular detector response.

9. A method for remotely determining concentrations of at least two exhaust gas constituents in a vehicle emission plume, comprising:
   directing radiation from a radiation source through an emission plume of a moving vehicle to a first filter and then to a detector, wherein the first filter is arranged on a rotatable filter wheel and is capable of filtering out radiation except for a first predetermined wavelength band;
   generating a first detector response indicative of the intensity of radiation received by the detector via the first filter;
   rotating the filter wheel such that the radiation from the radiation source is directed through the emission plume of the moving vehicle to a second filter arranged on the filter wheel and then to the detector, wherein the second filter is capable of filtering out radiation except for a second predetermined wavelength band;
   generating a second detector response indicative of the, intensity of radiation received by the detector via the second filter; and
   processing the first and second detector responses to provide information about the composition of the emission plume of the vehicle.

10. The method according to claim 9, further comprising:
    passing the radiation through a general filter, to remove substantially all light having a wavelength outside a predetermined broad detection band, after the radiation has passed through the emission plume of the vehicle, but before the radiation reaches the filter wheel.

11. The method according to claim 9, wherein the filter wheel and the detector are located within a housing which is sealed to substantially prevent radiation from reaching the detector except via one of the at least two filters.

12. The method according to claim 9, wherein the radiation source projects a beam of infrared radiation across the path of the moving vehicle.

13. The method according to claim 9, wherein one of the at least two filters comprises a pass through filter.

14. The method according to claim 9, wherein one of the at least two filters comprises a reflective filter.

15. A method for remotely determining concentrations of at least two exhaust gas constituents in a vehicle emission plume, comprising:
    directing radiation from a radiation source through an emission plume of a moving vehicle to a first filter and then to a detector, wherein the first filter is capable of filtering out radiation except for a first predetermined wavelength band;
    generating a first response indicative of the intensity of radiation received by the detector;
    altering the position of the detector such that the radiation from the radiation source may be directed through the emission plume to a second filter and then to the detector, wherein the second filter is capable of filtering out radiation except for a second predetermined wavelength band;
    generating a second response indicative of the intensity of radiation received by the detector via the second filter; and
    processing the first and second responses to provide information about the composition of the emission plume of the vehicle.

* * * * *

UNITED STATES PATENT AND TRADEMARK OFFICE
CERTIFICATE OF CORRECTION

PATENT NO. : 7,141,793 B2 Page 1 of 1
APPLICATION NO. : 09/840080
DATED : November 28, 2006
INVENTOR(S) : James H. Johnson et al.

It is certified that error appears in the above-identified patent and that said Letters Patent is hereby corrected as shown below:

On the title page, rewrite Item (54) as follows:

-- (54) REMOTE VEHICLE EMISSION SENSING
DEVICE WITH SINGLE DETECTOR --

Signed and Sealed this

Thirteenth Day of March, 2007

JON W. DUDAS
*Director of the United States Patent and Trademark Office*